(12) United States Patent
Robins

(10) Patent No.: US 7,981,364 B2
(45) Date of Patent: Jul. 19, 2011

(54) GAS DETECTION METHOD AND SYSTEM

(75) Inventor: Ian Robins, Dorchester (GB)

(73) Assignee: Honeywell Analytics AG, Uster (CH)

( * ) Notice: Subject to any disclaimer, the term of this patent is extended or adjusted under 35 U.S.C. 154(b) by 531 days.

(21) Appl. No.: 11/664,771

(22) PCT Filed: Dec. 6, 2005

(86) PCT No.: PCT/GB2005/004693
§ 371 (c)(1),
(2), (4) Date: Jan. 18, 2008

(87) PCT Pub. No.: WO2006/061607
PCT Pub. Date: Jun. 15, 2006

(65) Prior Publication Data
US 2008/0138911 A1 Jun. 12, 2008

(30) Foreign Application Priority Data

Dec. 7, 2004 (EP) .................................... 04257602

(51) Int. Cl.
G01N 7/00 (2006.01)
G01N 21/00 (2006.01)
G01N 27/00 (2006.01)
G01N 31/00 (2006.01)
G01N 33/00 (2006.01)

(52) U.S. Cl. ................ 422/83; 422/63; 422/64; 422/65; 422/85; 422/86; 436/43; 436/181; 436/164; 436/171

(58) Field of Classification Search .................... 422/85, 422/86, 63, 64, 65, 66
See application file for complete search history.

(56) References Cited

U.S. PATENT DOCUMENTS 3,036,893 A * 5/1962 Natelson ....................... 436/170
(Continued)

FOREIGN PATENT DOCUMENTS

EP 0 266 216 A 5/1988
(Continued)

OTHER PUBLICATIONS

International Search Report dated Feb. 21, 2006 issued by ISA, EPO, as published on Jun. 15, 2006 under Publication No. WO 2006/061607 A1.

(Continued)

Primary Examiner — Brian J Sines
(74) Attorney, Agent, or Firm — Husch Blackwell

(57) ABSTRACT

There is disclosed a method of operating a colorimetric gas detector system that comprises a substrate (1) bearing a material (12) that can react with a target gas to produce a change in the wavelength of radiation absorbed or transmitted by the material ("color-change material"). The method involves:

a) applying onto a region (15) of the substrate that includes color-change material a chemical of predetermined concentration that reacts directly or indirectly with the color-change material to produce a change in the wavelength of the radiation absorbed or transmitted by the material;

b) detecting the radiation absorbed or transmitted in said region (15) at a wavelength absorbed or transmitted by the reaction product of the color change material with the chemical, and c) generating a signal in accordance with the amount of radiation detected at the second wavelength, said signal being dependent on the amount of color-change material on the substrate.

The signal can be used to correct the reading of the color change material when exposed to target gas to compensate for varying amounts of color-change material on the substrate.

6 Claims, 2 Drawing Sheets

U.S. PATENT DOCUMENTS

| | | | |
|---|---|---|---|
| 3,368,872 A * | 2/1968 | Natelson | 422/66 |
| 3,502,438 A * | 3/1970 | Natelson | 422/66 |
| 3,607,079 A * | 9/1971 | Maxon et al. | 436/44 |
| 3,754,867 A * | 8/1973 | Guenther | 422/91 |
| 4,059,405 A * | 11/1977 | Sodickson et al. | 436/44 |
| 4,071,315 A * | 1/1978 | Chateau | 436/518 |
| 4,204,838 A * | 5/1980 | Atherton et al. | 436/44 |
| 4,336,031 A | 6/1982 | Hopmeier et al. | |
| 5,091,642 A * | 2/1992 | Chow et al. | 250/226 |
| 5,508,200 A * | 4/1996 | Tiffany et al. | 436/44 |
| 6,355,487 B2 * | 3/2002 | Kowallis | 436/44 |
| 6,387,331 B1 * | 5/2002 | Hunter | 422/102 |
| 6,635,415 B1 * | 10/2003 | Bollinger et al. | 435/4 |
| 6,689,319 B1 * | 2/2004 | Fisher et al. | 422/67 |
| 2005/0042136 A1 * | 2/2005 | Marganski et al. | 422/58 |

FOREIGN PATENT DOCUMENTS

| | | |
|---|---|---|
| EP | 1 266 944 A1 | 12/2002 |
| JP | 06 249 850 | 9/1994 |
| WO | WO 93/21928 A | 11/1993 |
| WO | WO 99/61892 | 12/1999 |

OTHER PUBLICATIONS

Written Opinion of the International Searching Authority (European Patent Office), Publication No. WO 2006/061607.

* cited by examiner

GAS DETECTION METHOD AND SYSTEM

TECHNICAL FIELD

The present invention relates to detectors, especially for detecting toxic gases. The detectors include a material that reacts with a gas or vapour, or a family of gases or vapours, being sensed (hereinafter referred to as a "target gas") and the reaction causes a change in the radiation absorption of the material, usually evidenced by a change in colour in the visible spectrum.

BACKGROUND ART

It is known to detect toxic gases using chemical cassettes having a paper tape substrate impregnated with a specific chemical material; the paper is usually absorbent and is impregnated with the chemical material by dipping it into a trough of a solution of the material. The tape is subsequently dried and installed in a cassette. During use, the paper tape is placed in an analyser that draws gas from the atmosphere being monitored through the tape. The chemical material absorbed on or in the tape is chosen to react with the target gas and to change colour; the degree of colour change, for exposure to a predetermined amount of atmospheric gas, provides a measure of the concentration of the target gas in the atmosphere being monitored. The analyser detects the change of colour, i.e. radiation absorbed or transmitted by the reaction product at a wavelength at which the unreacted colour change material absorbs or transmits to no extent or a lesser extent, and then calculates the gas concentration by comparing the colour change to a table of known gas responses that has been pre-programmed into the analyser. Periodically, the tape is advanced to bring a fresh length of tape to the position within the analyser through which the target gas is drawn to make a further measurement using the fresh length of tape. One major advantage of the tape system is that a permanent visual record exists of positive gas responses as seen by the visible colour change of the tape.

The colour-change response will give a measure of the amount of the target gas in the atmosphere being monitored. However the colour-change response will depend on the amount of colour-change material absorbed in or applied onto the tape, which in turn will depend on the amount of colour-change material applied to the substrate during manufacture and this can vary, depending on the control applied by the manufacturer. Secondly, the tape and the colour-change to material can degrade over time under conditions of temperature, humidity and/or light. Therefore the amount of colour-change material present will depend on the time that has elapsed since manufacture. Finally, the substrate is not necessarily uniform, either in its density or its absorptivity and different areas can absorb different amounts of the colour-change material. All these factors can lead to inaccuracies in the response to a given concentration of target gas both from tape to tape but also along the length of a single tape.

It is an object of the present invention to overcome or alleviate some or all of the above problems.

DISCLOSURE OF INVENTION

According to the present invention, there is provided a method of operating a colorimetric gas detector system that comprises a substrate bearing a material that can react with a target gas to produce a change in the wavelength of radiation absorbed or transmitted by the material (hereafter called "colour-change material"), wherein the method comprises:

a) applying onto a region of the substrate that includes colour-change material a chemical of predetermined concentration that directly or indirectly reacts with the colour-change material to produce a change in the wavelength of the radiation absorbed or transmitted by the material;

b) detecting the radiation absorbed or transmitted in said region at a wavelength ("second wavelength") absorbed or transmitted by the reaction product of the colour change material with the chemical, said second wavelength being a wavelength at which the unreacted colour change material absorbs or transmits to no extent or a lesser extent than the said reaction product; and c) generating a signal in accordance with the amount of radiation detected at the second wavelength, said signal being dependent on the amount of colour-change material on the substrate at that that specific point.

The signal can be used to correct the reading of the colour change material when exposed to target gas to compensate for varying amounts of colour-change material on the substrate.

The chemical may itself react with the colour change material or may react with one or more other components to form a product that reacts with the colour change material. The other component may already be provided on the substrate or may be applied as part of the same procedure as the chemical. For example, liquid A could be applied followed by liquid B that react together to produce a third material "C" that reacts with the colour change material. An example of this is to generate ammonia in solution you can deposit ammonium hydroxide (either as a solid or in a weakly alkaline solution) and then add a weak acid.

The apparatus will generally be set up to draw a predetermined amount of atmospheric gas though or over the colour change material, e.g. by operating a pump to draw gas for a preset time. The amount of chemical applied is preferably such that it produces a colour change in the colour change material that is within the range of colour changes that one would expect to see for anticipated target gas concentrations, taking into account the time that the atmospheric gas is drawn though or over the colour change material.

The signal from step c) can be used in a number of ways to confirm that the colorimetric gas detector system is operating properly and producing a reasonably accurate response. The method may include a step of comparing the signal with a predetermined range or threshold value and generating an to alarm signal indicating that the operation of the system is faulty if the measured signal falls outside the range or falls beyond the threshold.

The method may include the further steps of:

d) contacting a second region of the substrate with gas from the atmosphere, the second region being different from the region to which the chemical was applied in step a);

e) detecting the amount of radiation at a wavelength ("first wavelength") absorbed or transmitted by the reaction product of the colour change material with the target gas, said first wavelength being a wavelength at which the unreacted colour change material absorbs or transmits to no extent or a lesser extent than the said reaction product; and f) calculating the amount of target gas in the atmosphere from the radiation detected in step e), said calculation including adjusting the calculated amount of target gas in the atmosphere in accordance with the radiation detected in step b).

In this case, the calculation may be adjusted by using the signal from step c) to calibrate and/or zero the radiation detected in step e).

The second region that is used to measure the target gas is preferably adjacent to the region to which the chemical was applied in step a).

An especially important subsidiary aspect of this invention is that the chemical can be liquid since liquids are much cheaper and easier to store than gases, they are also easier to apply than gases, especially when applied to a given restricted location and it is easier and cheaper to meter precise doses of liquids.

Colorimetric gas detector systems are used primarily for measuring toxic gases, especially toxic gases that are difficult to sense electrochemically or at concentrations lower than can normally detectable by electrochemical techniques. These include hydrogen chloride, hydrogen bromide and hydrogen fluoride, ozone, arsine, phosphine, diborane and silane. The chemical used need not react with the colour-change material in a way corresponding to the way in which the intended target gas reacts with the colour-change material so long as the reaction with the chemical brings about a colour-change that is dependent on the amount of the colour-change material in the substrate. However, the chemical will often react in the same way as the target gas. For example, the colour-change material used for the detection of acidic or basic gases such as ammonia, hydrogen chloride, hydrogen bromide and hydrogen fluoride can be pH dependent, e.g. a pH indicator, and so the chemical used in such circumstances could also be a base, e.g. sodium hydroxide or ammonium hydroxide solution, or an acid, for example hydrochloric acid. Likewise, the colour-change material used for detecting ozone may be oxidised by the ozone to bring about the colour change and so the chemical used in this circumstance may be another oxidising agent, for example hydrogen peroxide or hypochlorous acid. For any of the hydrides, ammonia (or ammonium hydroxide) could be used.

The wavelength that is detected after the reaction of the colour change material with any target gas in the atmosphere (the first wavelength) may thus be the same as the wavelength that is detected after the reaction of the colour change material with the chemical (the second wavelength) and preferably they are the same wavelengths since that simplifies detection. However, it is conceivable that the first and second wavelengths could be different.

The chemical that is applied to the substrate may be a liquid reagent, optionally mixed with a diluent, a solution, a gel, an emulsion or a suspension.

The present invention also provides a colorimetric gas detector system for detecting and/or measuring the presence of a target gas in an atmosphere being monitored, the system comprising:
a) a gas sensing station configured to bring a sample of gas from the atmosphere into contact with a substrate that carries a colour-change material;
b) a holder configured to support the substrate and advance successive substrates or successive parts of the same substrate to the gas sensing station;
c) a chemical reservoir;
d) an applicator for applying a predetermined dose of a chemical from the reservoir onto a region of the substrate containing colour change material,
e) a radiation detector arranged to detect (i) the radiation absorbed or transmitted by the colour-change material to which the chemical is applied and (ii) the radiation absorbed or transmitted by the colour-change material that is contacted by gas from the atmosphere and then to generate signals in accordance with the radiation detected; and
f) a processor configured to process the signals from the radiation detector and calculate the amount of target gas in the atmosphere from the signal derived from the radiation detected at e)(ii).

The processor is preferably configured to adjust the calculation of the amount of target gas in the atmosphere using the signal derived from the radiation detected in e)(i), e.g. to calibrate the calculation of the amount of target gas using the signal derived from the radiation detected at e)(i).

The radiation detected at e)(i) and e(ii) is preferably restricted to the first and second wavelengths respectively.

The radiation detector may be a single detector arranged to detect radiation e)(i) and radiation e)(ii) or separate detectors for radiation e)(i) and radiation e)(ii).

The system may include an alarm generator, which may be part of the controller, arranged to compare the signal indicating the amount of the target gas with a predetermined range of acceptable values or a threshold value and to initiate an alarm routine if the signal falls outside the predetermined range or falls beyond the threshold. The alarm may be a visible and/or audible alarm, which may be part of the gas detector system or remote from the system (or indeed both).

The gas sensing station will generally include:
(a) a location at which the predetermined dose of the chemical from the reservoir is applied onto the substrate,
(b) a location at which gas from the atmosphere is drawn through or past the substrate,
(c) a location at which radiation that has been absorbed or transmitted by the colour-change material to which the chemical has been applied is detected and
(d) a location at which radiation that has been absorbed or transmitted by the colour-change material following exposure to gas from the atmosphere is detected.

These locations can all be the same or different; locations (a) and (b) will generally be different form each other and from locations (c) and (d). Locations (c) and (d) again can be different but they are preferably the same. When the to locations are different, they are preferably arranged adjacent to one another. The functions that are carried out at the gas sensing station can take place simultaneously for different substrates or regions of a single substrate or they can take place at different times.

One substantial advantage of the present invention is that the system can be calibrated simply and cheaply without having to provide a complex arrangement for feeding calibration gas to the system.

The applicator for applying a liquid chemical may be an inkjet printing head, which can accurately meter a required amount of liquid onto the substrate, is cheap and consumes a relatively small amount of power. However other applicators can be provided instead, for example tamper printing or use of a syringe dispenser.

Known gas detection systems having substrates carrying colour-change material are often set up to take readings of the target gas periodically; before each reading, the substrate is advanced to the gas sensing station (if the substrate can be used for multiple readings) or a fresh substrate is provided at the gas sensing station (if the substrate can be used for a single reading only).

This arrangement may be used in the present invention. The chemical can be applied to the substrate before each reading of the target gas content of the atmosphere being monitored or before every $n^{th}$ reading, where n is an integer greater than 1. The area to which the chemical is applied is preferably a part only of the substrate that is sensed by the radiation detector so that the changed radiation in the area resulting from the application of the chemical can be detected by the same equipment as detects the colour change due to the presence of target gas in the atmosphere being monitored. This arrangement means that the calibration reading can be taken close to the location where the actual target gas reading is taken which minimises the error due to variations in the concentration of the colour-change material on the substrate.

If the colour-change material is provided in discrete areas of the substrate then the chemical can be applied to part only of the discrete areas.

Preferably the system is controlled by a microprocessor, including one or more of the following functions: the advancement of the substrate, the drawing of the gas over or through the substrate, the reading of the changed wavelength of the colour-change material both in the areas to which chemical has been applied and those that are exposed to gas from the atmosphere being monitored, the application of the chemical, the alarm or calibration function and the printing, display and storage of the quantity of target gas detected.

In a preferred embodiment, the chemical is applied and the consequential change in radiation is sensed before the gas from the monitored atmosphere is drawn over or though the substrate since otherwise toxic gas in the atmosphere being monitored could affect the reading of the changed radiation in the area on which the chemical has been applied. Alternatively, the calibration step may only occur only after a positive gas reading (after alarm has occurred) to check the correct gas calibration. This procedure could rewind the tape (or other substrate) to a part of the tape before the part that gave rise to the positive reading and make a calibration and then repeating the procdure for a part of the substrate after the part that gave rise to the positive gas reading, thereby providing information on the amount of colour change material in the tape on both sides of the part that gave rise to the positive gas reading thereby providing even greater accuracy of the reading. This aspect may be very important to provide a permanent record of the dose of gas to which workers in a facility may have been exposed to.

Existing colorimetric gas sensors can be retrofitted to conform to the present invention.

This arrangement is especially advantageous with the system described in connection with our earlier co-pending European patent application no.04256223.1 filed 8 Oct. 2004.

More than one discrete area of colour-change material may be present on the substrate in the gas detection station at any one time, in which case each discrete area may be calibrated independently. More than one discrete area of colour-change material can be present at the gas sensing station in order to monitor the presence of more than one gas in the atmosphere concerned or in order to measure the amount of a cross-indication gas, i.e. a gas (other than the target gas) that causes a change in the colour change material.

The substrate may be a strip or tape, which may be housed in a cassette, so that sequential areas of the strip or tape are exposed to the atmosphere being monitored in the same arrangement as is currently used, as described above. In this case, the substrate could be gas porous to allow a sample of the gas from the monitored area to be drawn through it or it may be non-porous, in which gas the gas must be passed over the substrate. In addition, the substrate is preferably liquid-absorbent so that a liquid chemical applied is readily held by the substrate. However, it should not be so absorbent that the liquid migrates significantly from the place where it is deposited.

BRIEF DESCRIPTION OF DRAWINGS

The present invention will be described in further detail by way of example only by reference to the FIGS. 1 to 3 of the accompanying drawings in which.

DETAILED DESCRIPTION OF INVENTION

Figure 1:
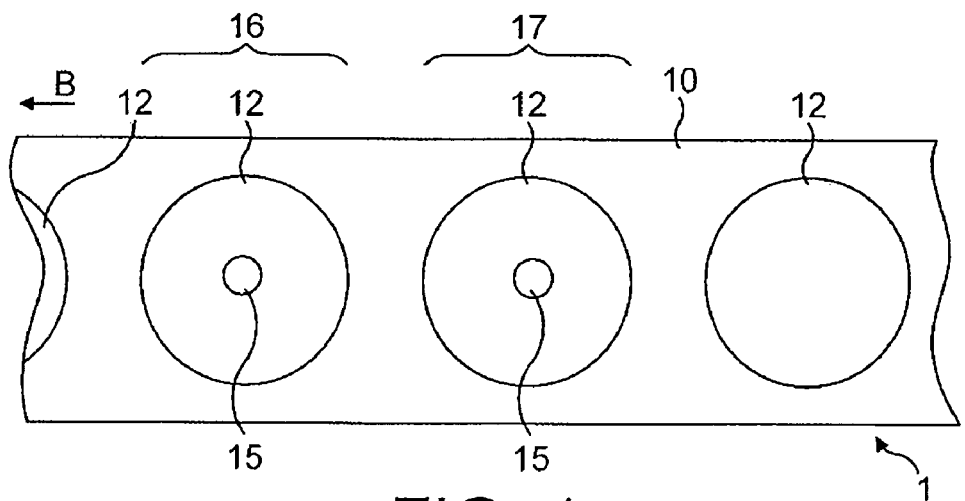
FIG. 1 shows a section of a tape used in accordance with the present invention.
Figure 2:
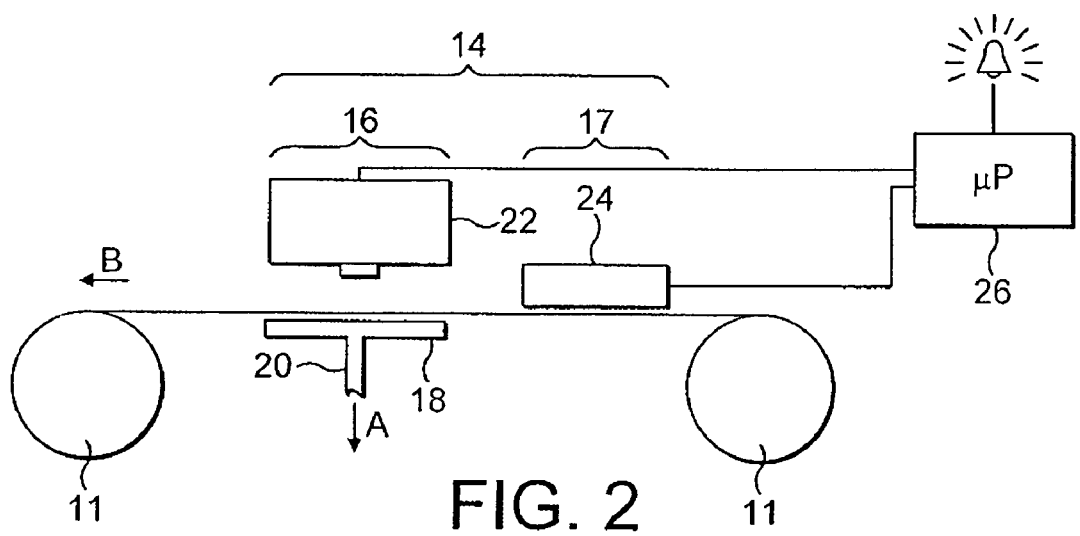
FIG. 2 is a schematic view of a colorimetric gas sensing apparatus in accordance with the present invention.

Referring initially to FIGS. 1 and 2, there is shown a tape that can be advanced between a holder, for example, two spools 11 in the direction of arrow "B" by a motor (not shown). The tape 10 is made up of a substrate 10, e.g. absorbent paper, on which are deposited regions of colour-change material, in this case dots 12; in FIG. 1, the dots are arranged in a single row but more than one row of dots 12 may be provided and different colour-change materials can be used in each of the rows. For example, the dots of one row may be made up of one type of colour-change material and the dots of a second row may be formed from different type of colour-change material for detecting a different target gas. The dots 12 may be formed on the substrate 10 by the manufacturer or deposited in situ by the user; in either case, they are suitably deposited by inkjet printing techniques.

The following colour change materials 1 to 3 may be used to form the dots 12.

Material 1

A solution in water or an organic solvent such as methanol that contains:

0.1 weight percent of eosine yellowish (colour index: acid red 87) which is a fluoscine based dye, 0.3 weight percent of para-toluenesulphonic acid, and 15 weight percent polyhydric alcohol such as glycerin, This material when dried is substantially transparent or very pale pink in colour because the pH of the material is maintained very low due to the acid (the dye only shows its colour when neutral or basic). This material can be used to detect the concentration of a basic gaseous component (such as ammonia) by the gas making the material more basic and therefore the natural colour of the dye can emerge. Colour change—clear to yellow Material 2

Same as Material 1 except that the eosine yellowish is replaced by rose benzal, phloxine, eosine bluish, or erythrosine. The para-toluenesulphonic acid may be replaced by naphthalenesulphonic acid or benzensulphonic acid. Material 2 is also used for the detection of basic gases.

Material 3

| | |
|---|---|
| Solvent: | 1.5 ml. conc. nitric acid; 25 ml. glycerol; and 224 ml. methanol. |
| Active ingredient: | 2.5 grams silver nitrate |
| Substrate: | a paper tape coated with silicic acid (or silica gel) |

This material can be used for detecting metal hydrides such as arsine, phosphine, diborane. On exposure to these materials, the deposited material undergoes a colour change from clear to grey/black. Instead of conc. nitric acid, other organic or inorganic acids may be used, e.g.

One of the acids mentioned in Materials 1 and 2 as previously described in to Materials 1 and 2. An alcohol (methanol) was selected as the solvent because it allows the tape to dry readily when processed relative to a water-based solution but other alcohols and solvents may be used, e.g. ethyl alcohol and isopropyl alcohol, although volatile solvents are preferred. The glycerol increases the adsorbent ability of the tape by keeping the tape moist enough to allow the intended reaction between incoming hydride gas and the tape reagents to occur; other glycols can be used, e.g. ethylene glycol, propylene glycol and trimethylene glycol. The use of methanol and glycerol, however, is preferred on the grounds of cost.

A tape on which the above Material 3 is deposited maintains a white background for at least six months under normal storage conditions at room temperature with protection from light. Even after six months, the tape can still displays sensitivity (±10%) to hydride gases.

A more generalised solvent for the silver nitrate active ingredient is 0.1-5% acid;
5-20% glycol; and
94.9-75% alcohol.

The apparatus includes a gas detection station 14; an applicator, for example, an inkjet printer 24 is provided at location 17 of the gas detection station and, under the control of a processor, for example, a microprocessor 26, applies on the central region 15 of each dot 12 a predetermined amount of a liquid held in a reservoir (not shown) within the printer. The printer may incorporate more than one inkjet printing heads to apply different liquids. The liquid reacts with the colour-change material of the dots 12 to bring about a colour change in the material. The liquid for materials 1 and 2 may be a buffered base, e.g. sodium hydroxide and the liquid for material 3 may be ammonium hydroxide.

In the gas detection station 14, downstream of the printer 24, is a location 16 at which a radiation detector, for example, detector 22 is provided that measures the radiation transmitted by the region 15 within the dot 12 at a wavelength that is absorbed or transmitted by the reaction product of the colour change material with the liquid and at which the unreacted colour change material does not absorbs or transmit radiation or does so to a lesser extent than the unreacted colour change material. The detector generates a signal to the microprocessor 26 that compares it with a pre-programmed look-up table. Since the liquid deposited in region 15 has a known concentration, the degree of colour change measured will depend on the concentration of the colour change material in the dot 12 and this information can be used to zero and/or calibrate the apparatus, as described below. The detector is also able to measure the radiation transmitted or absorbed by the dot 12 outside region 15, as will also be described below.

The detector 22 may be a photosensitive cell located behind suitable filters that restrict the radiation reaching the cell to that transmitted by the colour-change material after it has reacted with the target gas. The photosensitive cell may be a still or video camera that forms an image of the areas of dot 12 of colour change material, including the region 15, that has passed through the filters either in colour or in a greyscale. The brightness of the pixels forming the image of the areas can be used to assess the colour change, which can be recorded by the camera.

Also at location 16, there is provided a plenum chamber. As with existing colorimetric gas detection, gas from an atmosphere being monitored may be drawn through or past the or each dot 12 present at location 16 within the gas detection station 14. The plenum chamber 18 is connected to a source of reduced pressure, e.g. a pump (not shown), via a line 20, and this arrangement draws gas from the atmosphere being monitored through the tape substrate in the direction of the arrow "A". The pump is preferably controlled by the microprocessor 26.

Once a sample gas from the atmosphere being monitored has been drawn through or past the dots 12 at location 16, the radiation transmitted by the dot 12 is measured by the detector 22. Again a signal is generated that is fed to the microprocessor 26, which compares it with a pre-programmed look-up table. The measurement is taken at the wavelength of the colour change material following exposure to the target gas. Since the degree of colour-change at this wavelength will depend on the concentration of the target gas within the atmosphere, the transmitted colour is an indication of the concentration of the target gas. In order to measure the radiation transmitted by the colour-change material, the tape will be exposed to a source of suitable radiation, which may simply be ambient radiation.

The functioning of the apparatus is described below.

The dots 12 may be of any shape, e.g. round or square, and may be any size. Instead of dots, strips of the colour-change material may be used or the tape may be uniformly impregnated with a single colour-change material. The colour change material may be deposited by the inkjet printer or the substrate may be supplied by the manufacturer with the colour change material already applied.

If the ink jet printer 24 is used to deposit the dots 12 of colour-change material onto a blank substrate tape 10, the material deposited should be allowed to dry before having the liquid applied in the central region 15 of each dot. Although it is a possibility not to dry the tape before the application of the liquid in the central regions 15, this is likely to lead to inaccuracies in the measurements described below and so is not preferred.

Figure 3:
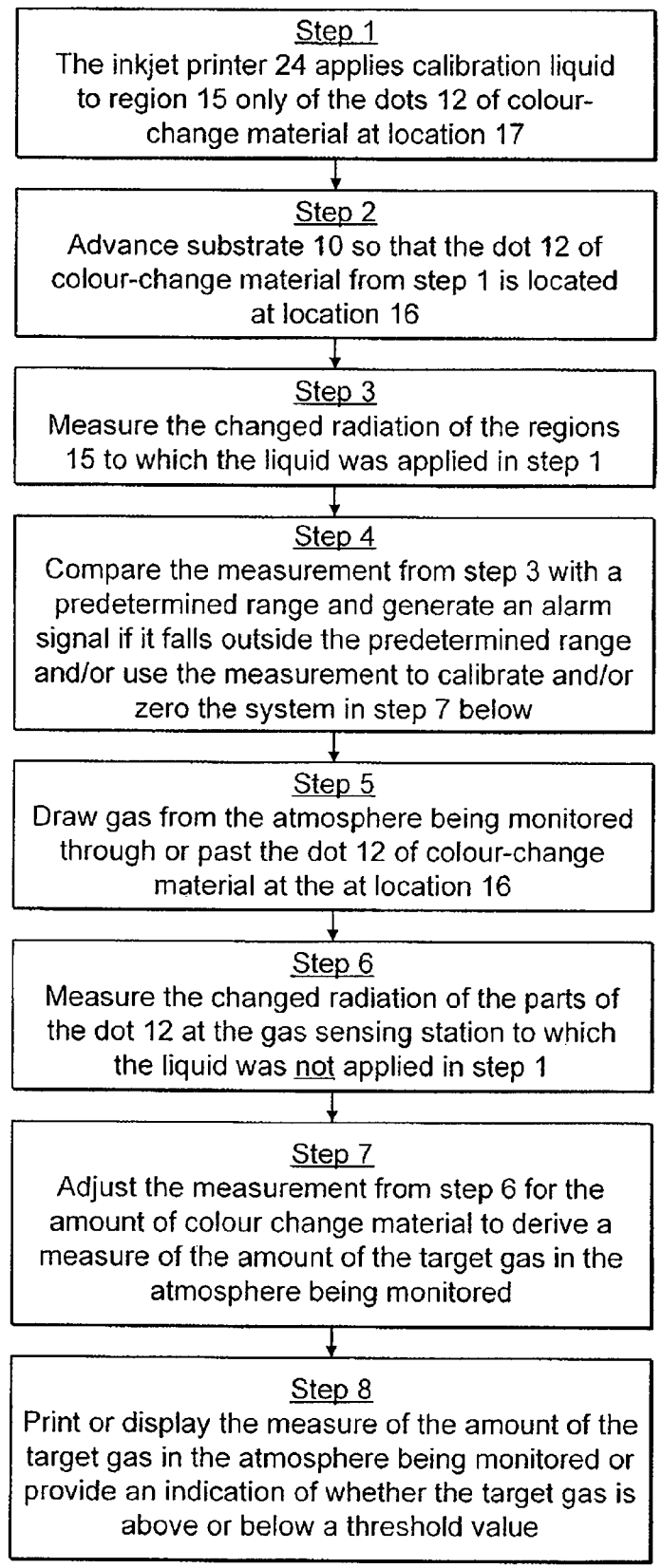
FIG. 3 is a flow chart showing the operation of the system of FIG. 2.

FIG. 3 is a flow diagram of the steps used for detecting a target gas using the tape shown in FIG. 1 and the apparatus shown in FIG. 2.

In step 1, the inkjet printer 24 applies a calibration liquid of known composition and concentration to the central region 15 of a dot 12 that is positioned at location 17 of the gas detection station 14 opposite the printer 24. This liquid causes the colour-change material in region 15 to change colour and the degree of colour change will depend on the amount of colour-change material in dot 12.

In step 2, the dot 12 is advanced from station 17 to station 16 opposite the light detector 22. The radiation from the central region 15 of dot 12 is measured by light detector 22, which is preferably a still or moving camera. This can be achieved by analysis of the pixels in the image of the region 15 of dot 12 in location 16 of the gas sensing station. Thus, for example, a filter can be placed between the substrate 10 and the camera 22 that transmits radiation at the wavelength of the colour-change material after it has changed colour due to the liquid. Then the intensity of the radiation transmitted can be measured either in greyscale or colour by the camera 16.

A signal is sent by the camera 22 to the microprocessor 26 providing a measure of the radiation transmitted by the area 15. This signal provides a measure of the degree of colour change in the dot 15 caused by the liquid applied at location 17 and hence a measure of the amount of colour-change material provided in the dot 15.

In step 4, the measurement obtained from step 3 can be used in two ways by the microprocessor. Firstly, it is possible to compare the measurement from step 3 with a predetermined range of values and generate an alarm signal that is fed to an alarm generator, for example, alarm 28 if the measurement falls outside the range. The concentration of the colour-change material in dot 12 should be controlled within a relatively narrow concentration range. When the liquid is applied by the inkjet printer 24, the intensity of the colour-change material in the regions 15 should therefore also fall within a narrow range. If the intensity measured falls outside that range, an error signal or an alarm signal is generated showing that the tape 10 being used is not within specification. This will allow the user to change the faulty tape with a fresh tape.

Alternatively or in addition, the magnitude of the signal from step 3, which is dependent on the amount of colour-change material in the dot 12, can be used to adjust the measurement made in step 7 below to take into account the concentration of colour-change material actually present on the substrate to provide a more accurate measure of the amount of target gas in the atmosphere being monitored, as described below.

In step 5, the pump is operated to draw air through line 20 in the direction of arrow "A", which causes a reduced pressure in plenum chamber 18. The reduced pressure in plenum chamber 18 causes air to be drawn from the atmosphere being monitored through the tape 10. Any target gas in the atmosphere will cause a change of colour in the colour-change material in the dot 12. The pump is operated for a predetermined time. The change of colour in the dot 12 (apart from the central region 15) is measured (step 6) by the camera 22 and a signal is fed to microprocessor 26, which is partly dependent on the amount of colour-change material that is actually deposited in the dot 12. The signal from step 3 gives a measure of the amount of colour-change materials in the dots and accordingly, in step 7, the measurement from step 3 is used adjust the measurement from step 6 to provide a final measurement of the amount of colour-change material present in the dots 12 at location 16. This will provide a more accurate measure of the amount of target gas in the atmosphere being monitored. The microprocessor can achieve this in a number of different ways, e.g. by applying a correction factor to the value of the amount of target gas measured in step 3 or by organising the lookup table to store target gas concentrations associated with the signals from step 3 for each of a variety of different signals from step 6. Both such arrangements will calibrate the output of the microprocessor in accordance with the amount of colour change material on the substrate.

In step 8, the amount of the target gas calculated in step 7 is printed, recorded or displayed on a printer, recorder or display (not shown). In addition or instead, the amount of target gas calculated from step 7 can be used to trigger an alarm generator, for example, the alarm 28 if it is above a threshold value.

Although the above description has been specifically described in relation to tape, it is not necessary that the substrate containing the discrete areas of colour-change material should be a tape and other formats can be used, for example an A4 sheet of paper.

The invention claimed is:

1. A colorimetric gas detector system for detecting and/or measuring the presence of a target gas in an atmosphere being monitored, the system comprising:

a) a gas sensing station configured to bring a sample of gas from the atmosphere into contact with a substrate that carries a colour-change material;
   b) a holder configured to support the substrate and advance successive substrates or successive parts of the same substrate to the gas sensing station;
   c) an applicator for applying a predetermined dose of a chemical held within the applicator onto a region of the substrate containing colour change material,
   d) a plenum chamber on a first side of the substrate, when the substrate is in the gas sensing station, the plenum chamber drawing gas from the atmosphere on a second side of the substrate to the first side of the substrate so that the gas travels through or past the region of the substrate containing the colour change material before entering the plenum chamber;
   e) a radiation detector downstream of the applicator and arranged to detect (i) the radiation absorbed or transmitted by the colour-change material carried by the substrate to which the chemical is applied and (ii) the radiation absorbed or transmitted by the colour-change material carried by the substrate that is contacted by gas from the atmosphere and then to generate signals in accordance with the radiation detected, the holder advances the region of the substrate containing the colour-change material from the applicator to the radiation detector; and
   f) a processor configured to process the signals from the radiation detector and calculate the amount of target gas in the atmosphere from the signal derived from the radiation detected at e)(ii).

2. A system as in claim 1, wherein the processor is configured to adjust the calculation of the amount of target gas in the atmosphere using the signal derived from the radiation detected in e)(i).

3. A system as in claim 1, wherein the processor is configured to calibrate the calculation of the amount of target gas using the signal derived from the radiation detected at e)(i).

4. A system as claimed in claim 1, which includes an alarm generator arranged to compare the signal generated by the processor with a predetermined range of acceptable values or a threshold value and to initiate an alarm routine if the signal falls outside the predetermined range or falls beyond the threshold value.

5. A system as in claim 1, wherein the processor is configured to control the applicator to apply chemical and to control the detector to detect radiation.

6. A system as in claim 4, wherein the processor is configured to control the applicator to apply chemical and to control the detector to detect radiation.

* * * * *